United States Patent [19]

Fuchs

[11] Patent Number: 4,873,369
[45] Date of Patent: Oct. 10, 1989

[54] PURIFICATION OF CYCLOHEXANONE OXIME CONTAINING AMMONIUM SULFATE

[75] Inventor: Hugo Fuchs, Ludwigshafen, Fed. Rep. of Germany

[73] Assignee: BASF Aktiengesellschaft, Ludwigshafen, Fed. Rep. of Germany

[21] Appl. No.: 22,235

[22] Filed: Mar. 5, 1987

[30] Foreign Application Priority Data

Mar. 11, 1986 [DE] Fed. Rep. of Germany ....... 3607997

[51] Int. Cl.$^4$ .......................................... C07C 131/00
[52] U.S. Cl. ................................................ 564/264
[58] Field of Search ......................................... 564/264

[56] References Cited

U.S. PATENT DOCUMENTS

| | | | |
|---|---|---|---|
| 2,820,825 | 1/1958 | Hillyer et al. | 564/264 X |
| 3,303,216 | 2/1967 | Nitsch et al. | |
| 3,625,835 | 12/1971 | Sittard et al. | 203/78 |
| 3,941,840 | 3/1976 | Rotaru | 564/264 X |
| 4,256,668 | 3/1981 | Mathew et al. | 564/264 X |

FOREIGN PATENT DOCUMENTS

| | | | |
|---|---|---|---|
| 2304766 | 8/1974 | Fed. Rep. of Germany . | |
| 1088220 | 10/1967 | United Kingdom | 564/264 |

*Primary Examiner*—Paul J. Killos
*Attorney, Agent, or Firm*—Keil & Weinkauf

[57] ABSTRACT

Cyclohexanone oxime containing ammonium sulfate is purified by a process in which cyclohexanone oxime in the molten state is passed over an acidic ion exchanger and a basic ion exchanger.

3 Claims, No Drawings

PURIFICATION OF CYCLOHEXANONE OXIME CONTAINING AMMONIUM SULFATE

Cyclohexanone oxime is produced on a large industrial scale by reacting cyclohexanone with aqueous hydroxylammonium sulfate solution at above the melting point of the cyclohexanone oxime. The cyclohexanone oxime melts thus obtained still contain about 5–8% by weight of water, as well as ammonium sulfate, some of which originates from the hydroxylamine synthesis and some from the neutralization during oximation. These amounts of ammonium sulfate tend to crystallize out when the water content of the cyclohexanone oxime is reduced in order to consume as little oleum as possible in the preparation of caprolactam. This leads to blockage of the nozzles during further processing to caprolactam. Similarly to the process described in German Pat. No. 2,029,114, a water-immiscible solvent is concomitantly used in the preparation of cyclohexanone oxime. However, recovery of the solvent is technically complicated, apart from the unavoidable solvent losses. In another process, described in German Published Application DE-AS 1,768,210, cyclohexanone oxime is said to be washed thoroughly with demineralized water. Apart from the fact that the water content increases and leads to increased consumption of oleum, problems are encountered in the separation of cyclohexanone oxime from the demineralized water.

It is an object of the present invention to provide cyclohexanone oxime which has a low content of ammonium sulfate and can be further processed to caprolactam without a salt separating out.

We have found that this object is achieved by a process for the purification of cyclohexanone oxime containing ammonium sulfate, wherein cyclohexanone oxime in the molten state is passed over an acidic ion exchanger and a basic ion exchanger.

The novel process has the advantages that ammonium sulfate is removed from the cyclohexanone oxime in a simple manner without the water content increasing or separation problems being encountered, the cyclohexanone oxime obtained does not lead to blockage of the feed nozzles when used for the preparation of caprolactam, and cyclohexanone oxime prepared in this manner can be further dried without a salt separating out.

According to the invention, the starting material used is cyclohexanone oxime containing ammonium sulfate. As a rule, such a cyclohexanone oxime contains from 5 to 8% by weight of water and from 10 to 1000 mg of ammonium sulfate per kg of cyclohexanone oxime. In addition to cyclohexanone oxime, small amounts of cyclohexanone, eg. from 10 to 1000 mg per kg, may also be present. Such a cyclohexanone oxime is obtained, for example, by a process described in German Pat. No. 1,205,966, if necessary by addition or partial removal of water with concentrated ammonium sulfate solution as described in German Pat. No. 2,138,930.

According to the invention, cyclohexanone oxime in the molten state is passed over an acidic ion exchanger and a basic ion exchanger. Advantageously, the cyclohexanone oxime is kept at from 70° to 95° C. Weakly acidic ion exchangers, for example crosslinked polymers containing carboxyl groups, are preferably used. These are composed, for example, of crosslinked polyacrylate containing carboxyl groups. It is also advantageous to use weakly basic ion exchangers. Examples of suitable ion exchangers are those composed of crosslinked polystyrene which contains primary, secondary or tertiary amino groups. It has proven particularly useful to pass molten cyclohexanone oxime first over a weakly acidic ion exchanger and then over a weakly basic one. However, a combination of weakly basic/weakly acidic/weakly basic ion exchangers is also possible.

When the ion exchangers are exhausted, they are reactivated in a conventional manner, for example with an acid, such as sulfuric acid, or a base, such as ammonia water or aqueous sodium hydroxide solution.

The cyclohexanone oxime thus obtained, which still contains residual water, for example from 5 to 8% by weight of water, can be further dried without problems, for example down to a water content of 3% by weight, by treating the melt with hot inert gases by the methods described in German Published Application DAS No. 1,034,629.

The novel process gives cyclohexanone oxime which contains ammonium sulfate in an amount of <5 mg/kg.

The Example which follows illustrates the process according to the invention.

EXAMPLE 75 ml of a weakly acidic ion exchanger composed of polyacrylate containing carboxyl groups are introduced into a cylindrical glass tube which has a diameter of 30 mm, is provided with a heating jacket and contains a frit at the lower end. A second ion exchanger column having the same diameter, likewise provided with a heating jacket and filled with 100 ml of a weakly basic ion exchanger composed of crosslinked polystyrene possessing tertiary amino groups is connected downstream of the first column. Both ion exchanger columns are brought to 80° C. Thereafter, 300 g/h of molten cyclohexanone oxime having a water content of 5% (m/m), a residual cyclohexanone content of 50 mg/kg and an ammonium sulfate content of 80 mg/kg are passed over the ion exchanger columns. The cyclohexanone oxime discharged from the exchanger column contains 5% (m/m) of water, 55 mg/kg of cyclohexanone and only 3 mg/kg of ammonium sulfate. This oxime can be brought to the desired water content by treatment with air or with $N_2$, without problems due to precipitated ammonium sulfate being encountered.

I claim:

1. A process for the purification of cyclohexanone oxime containing from 5 to 8% by weight of water and containing from 10 to 1000 mg of ammonium sulfate per kg of cyclohexanone oxime, wherein the cyclohexanone oxime in the molten state is passed over an acidic ion exchanger and a basic ion exchanger at a temperature from 70° to 95° C.

2. The process of claim 1, wherein weakly acidic and weakly basic ion exchangers are used.

3. The process of claim 1, wherein the molten cyclohexanone oxime is passed first over a weakly acidic ion exchanger and then over a weakly basic ion exchanger.

* * * * *